United States Patent
Degenhardt

(10) Patent No.: US 8,114,351 B2
(45) Date of Patent: Feb. 14, 2012

(54) ANALYSIS SYSTEM AND METHOD FOR THE ANALYSIS OF A BODY FLUID SAMPLE FOR AN ANALYTE CONTAINED THEREIN

(75) Inventor: Volker Degenhardt, Heppenheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/275,707

(22) Filed: Nov. 21, 2008

(65) Prior Publication Data
US 2009/0137062 A1     May 28, 2009

(30) Foreign Application Priority Data
Nov. 24, 2007 (EP) ..................... 07022814

(51) Int. Cl.
*G01N 21/00* (2006.01)
(52) U.S. Cl. ............ 422/82.05; 422/68.1; 422/503; 422/510
(58) Field of Classification Search ............ 422/50, 422/412, 414, 401, 417, 68.1, 81, 82.05, 422/82.07, 82.08, 82.09, 500, 501, 502, 503, 422/504, 506, 507, 509, 510, 511, 515, 525, 422/526; 436/174, 180
See application file for complete search history.

(56) References Cited

U.S. PATENT DOCUMENTS
4,713,974 A    12/1987   Stone
5,746,982 A *   5/1998   Saneii et al. ................ 422/134
2002/0001848 A1    1/2002   Bedingham et al.
2003/0143114 A1 *   7/2003   Andersson et al. ........... 422/64
2004/0265172 A1 *   12/2004   Pugia et al. .................. 422/58

FOREIGN PATENT DOCUMENTS
WO    2007005076 A1    1/2007
WO    2007106013 A1    9/2007

OTHER PUBLICATIONS

Lai, Siyi et al. "Design of a compact disk-like microfluidic platform for enzyme-linked immunosorbent assay." Analytical Chemistry (2004) 76 p. 1832-1837.*
Madou, Marc J. et al. "Design and fabrication of CD-like microfluidic platforms for diagnostics: microfluidic functions." Biomedical Microdevices (2001) 3 p. 245-254.*
Steigert, J. et al. "Integrated sample preparation, reaction, and detection on a high-frequency centrifugal microfluidic platform." Journal of the Association for Laboratory Automation (2005) 10 p. 331-341.*
European Search Report dated Aug. 5, 2008.

* cited by examiner

*Primary Examiner* — Yelena G Gakh
*Assistant Examiner* — Christopher A Hixson
(74) *Attorney, Agent, or Firm* — Dinsmore & Shohl LLP

(57) ABSTRACT

Analysis system and method for the analysis of a body fluid sample for an analyte contained therein are disclosed. The analysis system has a dosing station for dosing a liquid into a test element through a sample supply opening, which reacts with a reagent system present in a sample analysis channel of the test element. The analysis system also has a measurement station for measuring a measurement variable characteristic of the reaction at the measuring zone of a test element for the analytical result. The test element also includes a separate flushing liquid supply opening and a flushing liquid collection chamber which are in fluid communication to one another via a flushing liquid channel. The flushing liquid channel and the sample analysis channel differ from one another in such a manner that a liquid flowing through the flushing liquid channel does not reach the measuring zone.

17 Claims, 3 Drawing Sheets

ANALYSIS SYSTEM AND METHOD FOR THE ANALYSIS OF A BODY FLUID SAMPLE FOR AN ANALYTE CONTAINED THEREIN

FIELD OF THE INVENTION

The present invention relates generally to analysis systems and methods thereof, and in particular to a system and method for analyzing a body fluid sample for an analyte contained therein for medical purposes.

BACKGROUND OF THE INVENTION

Two classes of analysis systems are known in the field of medical analysis: wet analysis systems, and dry-chemical analysis systems. Wet analysis systems, which essentially operate using "wet reagents", perform an analysis via a number of required step such as, for example, providing a dosing sample and a reagent into a reagent vessel, mixing the dosing sample and reagent together in the reagent vessel, and measuring and analyzing the mixture for a measurement variable characteristic to provide a desired analytical result (analysis result). Such steps are performed using technically complex, large, line-operated analysis instruments, which allow required manifold movements of participating elements. This class of analysis system is typically used in large medical-analytic laboratories.

On the other hand, dry-chemical analysis systems operate using "dry reagents" which are typically integrated in a test element and implemented as a "test strip", for example. When these dry-chemical analysis systems are used, the liquid sample dissolves the reagents in the test element, and the reaction of sample and reagent results in a change of a measurement variable, which can be measured on the test element itself. Above all, optically analyzable (in particular colorimetric) analysis systems are typical in this class, in which the measurement variable is a color change or other optically measurable variable. Electrochemical systems are also typical in this class, in which an electrical measurement variable characteristic for the analysis, in particular an electrical current upon application of a defined voltage, can be measured in a measuring zone of the test element using electrodes provided in the measuring zone.

The analysis instruments of the dry-chemical analysis systems are usually compact, portable, and battery-operated. The systems are used for decentralized analysis, for example, at resident physicians, on the wards of the hospitals, and in so-called "home monitoring" during the monitoring of medical-analytic parameters by the patient himself (in particular blood glucose analysis by diabetics).

In wet analysis systems, the high-performance analysis instruments allow the performance of more complex multistep reaction sequences ("test protocols"). For example, immunochemical analyses often require a multistep reaction sequence, in which a "bound/free separation" (hereafter "b/f separation"), i.e., a separation of a bound phase and a free phase, is necessary. According to one test protocol, for example, the probe can first be transported through a porous solid matrix, which contains a specific binding reagent for the analyte. A marking reagent can subsequently be caused to flow through the porous matrix, to mark the bound analyte and allow its detection. To achieve precise analysis, a washing step must previously be performed, in which unbound marking reagent is completely removed. Numerous test protocols are known for determining manifold analytes, which differ in manifold ways, but which share the feature that they require complex handling having multiple reaction steps, in particular also a b/f separation possibly being necessary.

Test strips and similar analysis elements normally do not allow controlled multistep reaction sequences. Test elements similar to test strips are known, which allow further functions, such as the separation of red blood cells from whole blood, in addition to supplying reagents in dried form. However, they normally do not allow precise control of the time sequence of individual reaction steps. Wet-chemical laboratory systems offer these capabilities, but are too large, too costly, and too complex to handle for many applications.

To close these gaps, analysis systems have been suggested which operate using test elements which are implemented in such a manner that at least one externally controlled (i.e., using an element outside the test element itself) liquid transport step occurs therein ("controllable test elements"). The external control can be based on the application of pressure differences (overpressure or low-pressure) or on the change of force actions (e.g., change of the action direction of gravity by attitude change of the test element or by acceleration forces). The external control is especially frequently performed by centrifugal forces, which act on a rotating test element as a function of the velocity of the rotation.

Analysis systems having controllable test elements are known and typically have a housing, which comprises a dimensionally-stable plastic material, and a sample analysis channel enclosed by the housing, which often comprises a sequence of multiple channel sections and chambers expanded in comparison to the channel sections lying between them. The structure of the sample analysis channel having its channel sections and chambers is defined by profiling of the plastic parts. This profiling is able to be generated by injection molding techniques or hot stamping, microstructures, which are generated by lithography methods, increasingly being used more recently, however.

Analysis systems having controllable test elements allow the miniaturization of tests which have only been able to be performed using large laboratory systems. In addition, they allow the parallelization of procedures by repeated application of identical structures for the parallel processing of similar analyses from one sample and/or identical analyses from different samples. It is a further advantage that the test elements can typically be produced using established production methods and that they can also be measured and analyzed using known analysis methods. Known methods and products can also be employed in the chemical and biochemical components of such test elements.

In spite of these advantages, there is a further need for improvement. In particular, analysis systems which operate using controllable test elements are still too large. The most compact dimensions possible are of great practical significance for many intended applications.

SUMMARY OF THE INVENTION

It is against the above background that the present invention provides an analysis system having controllable test elements, which is distinguished by a compact and simple construction and by high user friendliness.

In one embodiment, an analysis system for the analysis of a body fluid sample for an analyte contained therein is disclosed and comprises a test element having a housing and a sample analysis channel enclosed by the housing, the sample analysis channel including a sample supply opening and a measuring zone. An analysis instrument having a dosing station is provided for dosing a liquid into the test element, which is located on the analysis instrument. The analysis instrument has a measurement station for measuring a measurement variable, which is characteristic for an analytical result at the measuring zone of the test element, which is located in a measuring position. The test elements is adapted for reacting a body fluid sample supplied through the sample supply opening with a reagent system present in the sample analysis channel and whereby the reaction of the body fluid sample with the reagent system results in a change of the measurement variable characteristic for the analytical result in the measuring zone. The test element includes a flushing liquid supply opening, which is separate from the sample supply opening, and a flushing liquid collection chamber. The flushing liquid supply opening and the flushing liquid collection chamber are in fluid communication to one another via a flushing liquid channel. The flushing liquid channel and the sample analysis channel are separate such that a liquid flowing through the flushing liquid channel does not reach the measuring zone.

In another embodiment, a test element for an analysis system providing an analysis of a body fluid sample for an analyte contained therein is disclosed. The test element comprises a housing, and a sample analysis channel enclosed by the housing. The sample analysis channel includes a sample supply opening for receiving the body fluid sample, a reagent system for reacting with the received body fluid sample, and a measuring zone which provides a change of a measurement variable characteristic for an analytical result when the body fluid sample reacts with the reagent system. The test element also has a flushing liquid collection chamber positioned in the housing, a flushing liquid supply opening separate from the sample supply opening, and a flushing liquid channel providing fluid communication between the flushing liquid supply opening and the flushing liquid collection chamber, wherein the flushing liquid channel and the sample analysis channel are separate such that a liquid flowing through the flushing liquid channel does not reach the measuring zone.

In still another embodiment, a method for delivering a liquid into a test element using an analysis system, which includes an analysis instrument and test elements, is disclosed. The analysis instrument has a dosing station for dosing a liquid into a test element, which is located on the analysis instrument, and the test elements each have a sample analysis channel, which includes a sample supply opening and a measuring zone. The test elements each include a flushing liquid supply opening, which is separate from the sample supply opening, and a flushing liquid collection chamber. The flushing liquid supply opening is in fluid communication to the flushing liquid collection chamber via a flushing liquid channel. The method comprises flushing the dosing station using a flushing liquid, the flushing liquid flowing into the flushing liquid supply opening of the test element and being collected in the flushing liquid collection chamber.

These and other features and advantages of the present invention will further become apparent from the drawings and detailed description provided hereafter.

BRIEF DESCRIPTION OF THE INVENTION

The following detailed description of the embodiments of the present invention can be best understood when read in conjunction with the following drawings in which.

DETAILED DESCRIPTION

Figure 1:
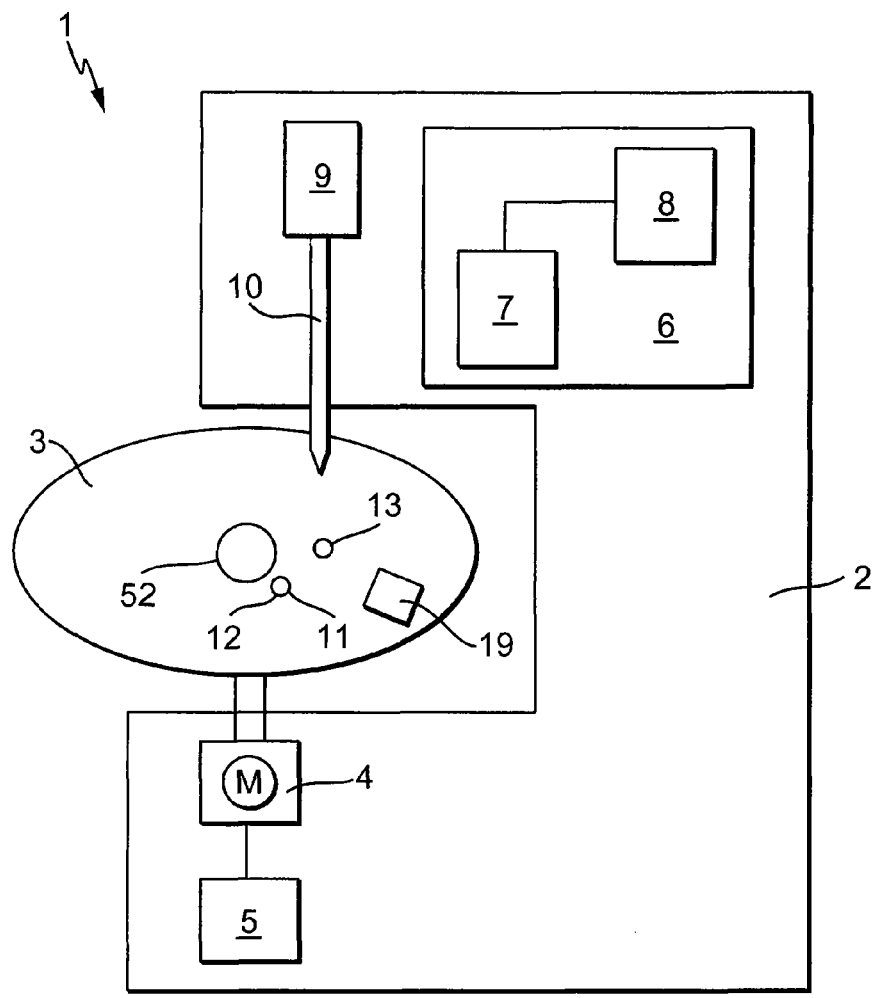
FIG. 1 shows a schematic illustration of the analysis system according to the invention.

The following description of the preferred embodiments of the invention is merely exemplary in nature and is in no way intended to limit the invention or its application or uses.

The analysis system according to the various embodiments of the invention generally provides a test element and an analysis instrument having a dosing station and a measurement station. The test element has a housing and (at least) one sample analysis channel enclosed by the housing, which includes a sample supply opening at its beginning and one or more measuring zones at its end.

A liquid is dosed into a test element using the dosing station of the analysis instrument. The dosing station typically has a dosing pump, such as a piston pump, and a tube for injecting the liquid, which is referred to as a dosing needle. The liquid can particularly be a liquid necessary for performing the reaction, such as a reagent solution, a washing solution, a dilution buffer, or a buffer solution, or the like. The body fluid sample to be determined can also be dosed using the dosing station in one embodiment, or supplied manually, for example, in another embodiment using a manual pipette or syringe.

The liquid can be dispensed into the sample supply opening of the test element or into one or more other (additional) supply openings of the test element. A measurement variable characteristic for the analytical result is measured using the measurement station at the measuring zone of the test element, wherein the test element being located in a measuring position. The measuring position in one embodiment corresponds to the sample dispensing position of the test element, however, in one specific embodiment the test element is moved between sample dispensing and measuring, so that both positions are different.

The test elements are implemented in such a manner that a body fluid sample supplied through a sample supply opening reacts with a reagent system which is provided in the sample analysis channel. The body fluid sample is a liquid of the body, such as blood, or a liquid sample, in which materials of the (human) body, such as tissue pieces, stool, or sputum are dissolved. The reaction of the body fluid sample with the reagent system results in a change of the measurement variable characteristic for the analytical result.

The test elements include a flushing liquid supply opening, separate from the sample supply opening, and a flushing liquid collection chamber, which are in fluid communication to one another via a flushing liquid channel. The flushing liquid channel and the sample analysis channel are separate from one another in such a manner that a liquid flowing through the flushing liquid channel does not reach the measuring zone of the sample analysis channel.

Before the dosing of the liquids from the dosing station into a dispensing opening of the test element, it is typical to conduct a flushing liquid through the dosing station, in particular its dosing needle. It is thus ensured that any air possibly present escapes and underdosing does not occur during the subsequent dosing. In particular, for example, during longer usage breaks, air bubbles can be formed or solid particles, such as salts, can accumulate by drying. The flushing also has a cleaning action. Preparatory flushing of this type is referred to in the professional world as "priming" and is applied in medical diagnostics upon any form of liquid delivery (dispensing, pipetting, or dilution).

The flushing liquid is taken from a reservoir container of the analysis instrument, supplied to the dosing unit, collected in a flushing liquid container in the analysis instrument, and disposed of. A design capable of disposing of the flushing liquid in a instrument-side collection container is known, for example, from U.S. Pat. No. 4,713,974.

It has been established in the context of the invention that the analysis system can be constructed significantly more compactly and simply if the flushing liquid is not disposed of in a collection container of the analysis instrument, but rather is dispensed directly into a special channel structure of the test element, which is also referred to hereafter as the "priming structure".

The fact that the flushing liquid (which can also be referred to as priming liquid) has always been collected until now in a instrument-side (device-side) collection container is to be explained in that the priming is a instrument function which is completely independent of the analysis steps which are performed using the test element. The test element is thus used in an alienated manner (not corresponding to its original purpose). It has been established in the context of the invention that this alienated use of the analysis system is possible and advantageous.

A decreased overall size of the analysis instrument results because no space is required for the collection container in the instrument and no fluid structures or fluid lines have to be provided for the transport of the flushing liquid into the waste container. Not only space is thus saved, but rather also costs in the production and upon service of the analysis instrument are saved.

In addition, monitoring the fill level of the collection container to avoid an overflow is dispensed with. On the one hand, monitoring electronics can thus be dispensed with, which prevent further processing using the analysis system if a limiting volume in the collection container is exceeded. On the other hand, dispensing with a instrument-side collection container results in increased service comfort for the user, because emptying the collection container by the user is dispensed with. Rather, the collection container positioned on the test element is automatically disposed of with the disposal of the used test element.

A further advantage of the analysis system according to the invention having a priming structure in the test element is that problems due to aging waste quantities in the collection container of the analysis instrument are avoided.

The term "flushing liquid" is understood as any liquid which is capable of flushing the dosing station, in particular its needle. The flushing liquid can additionally also fulfill other purposes. It can simultaneously be a washing liquid or a buffer liquid, which is used, for example, to dissolve reagents, wash off excess reaction participants, or dilute the sample. The body fluid to be determined or another liquid analysis sample (at least parts thereof) can also be used as the flushing liquid.

The flushing liquid supply opening, the flushing liquid collection chamber, and a flushing liquid channel connecting them are included under the term priming structure. The priming structure can additionally comprise further elements, in particular a valve for ventilating the flushing liquid collection chamber. The priming structure of the test element according to the invention includes a flushing liquid collection chamber whose volume is significantly less than the volume of the collection chamber provided until now in the analysis instruments, because the flushing liquid collection chamber of the test element must only accommodate a smaller quantity of flushing liquid, in particular the quantity of a single test. The flushing liquid collection chamber is in one embodiment implemented in such a manner that it only has the volume for one priming procedure. This volume is typically a few microliters (e.g., 20-30 μl). The quantity of the flushing liquid is just large enough to remove bubbles from the dosing needle and the dosing pump.

Alternatively, the volume of the flushing liquid collection chamber can also be greater than the volume of the flushing liquid, which is required for a single flushing. The chamber volume is typically enlarged if multiple priming procedures are executed, if a test element can be used for multiple analyses, for example, if a flushing procedure is to occur between two different samples or if multiple identical samples are analyzed using one test element and mixing of the sample liquids must be avoided.

The flushing liquid channel and the sample analysis channel are separated from one another in such a manner that an impairment of the analysis by the flushing liquid is avoided. In addition, a liquid which flows through the sample analysis channel from the sample supply opening in a predefined flow direction to the measuring zone does not reach the flushing liquid channel before it flows into the measuring zone. In one embodiment, a liquid flowing through the sample analysis channel can reach the flushing liquid channel or the flushing liquid collection chamber after flowing through the measuring zone, however.

In another embodiment of the analysis system according to the invention, the flushing liquid collection chamber of the test element contains a porous, absorbent matrix. The flushing liquid is sucked out of the flushing liquid channel by the occurring capillary effect. A reliable absorption of the flushing liquid in the flushing liquid collection chamber is ensured in this way.

An optical measurement in one embodiment is performed at the measuring zone of the test element, the known measuring methods for determining an analyte in a measuring zone being used. The optical measurement in one embodiment is a fluorescence measurement.

The above disclosed various embodiments of the invention are now described in greater details hereafter with reference made first to FIG. 1.

FIG. 1 shows an analysis system 1 according to an embodiment on the invention, which comprises an analysis instrument 2 and a controllable (disposable) test element 3.

The analysis instrument 2 has a drive 4 for moving the test element 3 around an axis of rotation. The transport of the sample liquid and other liquids in the test element 3 is externally controlled by the rotational movement of the test element 3. The rotational direction and the rotational velocity of the drive are regulated by controlling the drive 4 by means of a drive controller 5. The flow velocity, the flow direction, and the dwell time of the liquids in specific sections of the test element 3 can thus also be determined.

The analysis instrument 2 includes a measurement station 6, which comprises an optical measurement apparatus 7 and an analysis unit 8 to determine a characteristic measurement variable for the analytical result in the sample liquid at a measuring zone of the test element 3.

The optical measurement apparatus 7 in one embodiment comprises a measuring device for fluorescence measurement using locally resolved detection. In another embodiment, for a two-dimensional analysis optic, an LED or a laser is used to illuminate the measuring zone of the test element 3 and/or to excite optically detectable markings in the test zone. The detection in one embodiment is performed via a CCD optic or a CMOS optic. Of course, other optical measuring methods known in the prior art can also be applied in still other embodiments to measure the characteristic measurement variable.

In one embodiment, a dosing station 9 has a dosing needle 10 to apply a liquid in the test element 3. The dosing station 9 can comprise one or more liquid reservoirs (not shown here) for this purpose, in which the liquid or liquids to be applied are stored. The sample liquid or another liquid, such as a washing solution or a washing buffer, is dosed in a supply opening 11 of the test element 3 using the dosing station 9. In the test element 3 according to FIG. 1, the supply opening 11 is a sample supply opening 12 of the sample analysis channel (not shown here) of the test element 3.

In another embodiment, for simple and small analysis systems 1, the liquid sample to be determined is introduced manually by the user using a pipette into the sample supply opening 12, which is in one embodiment proximal to the axis of rotation. For dosing the body fluid sample into the sample delivery opening, the test element 3 is located in a sample dispensing position on the analysis instrument 14. In this case, the dosing station 9 is only used for delivering a washing solution in the supply opening 11.

To dose the most precise possible volume using the dosing station 9, the dosing station 9 and the dosing needle 10 is flushed using a flushing liquid in a preparatory step. The flushing liquid flowing through the dosing needle 10 is disposed of in a flushing liquid supply opening 13 of the test element 3. The test element 3 is located in a disposal position, in which the flushing liquid supply opening 13 is located below the dosing needle 10. This preparatory priming prevents air bubbles possibly present in the dosing station 9 or the dosing needle 10 from resulting in underdosing of the liquid to be dosed.

Figure 3:
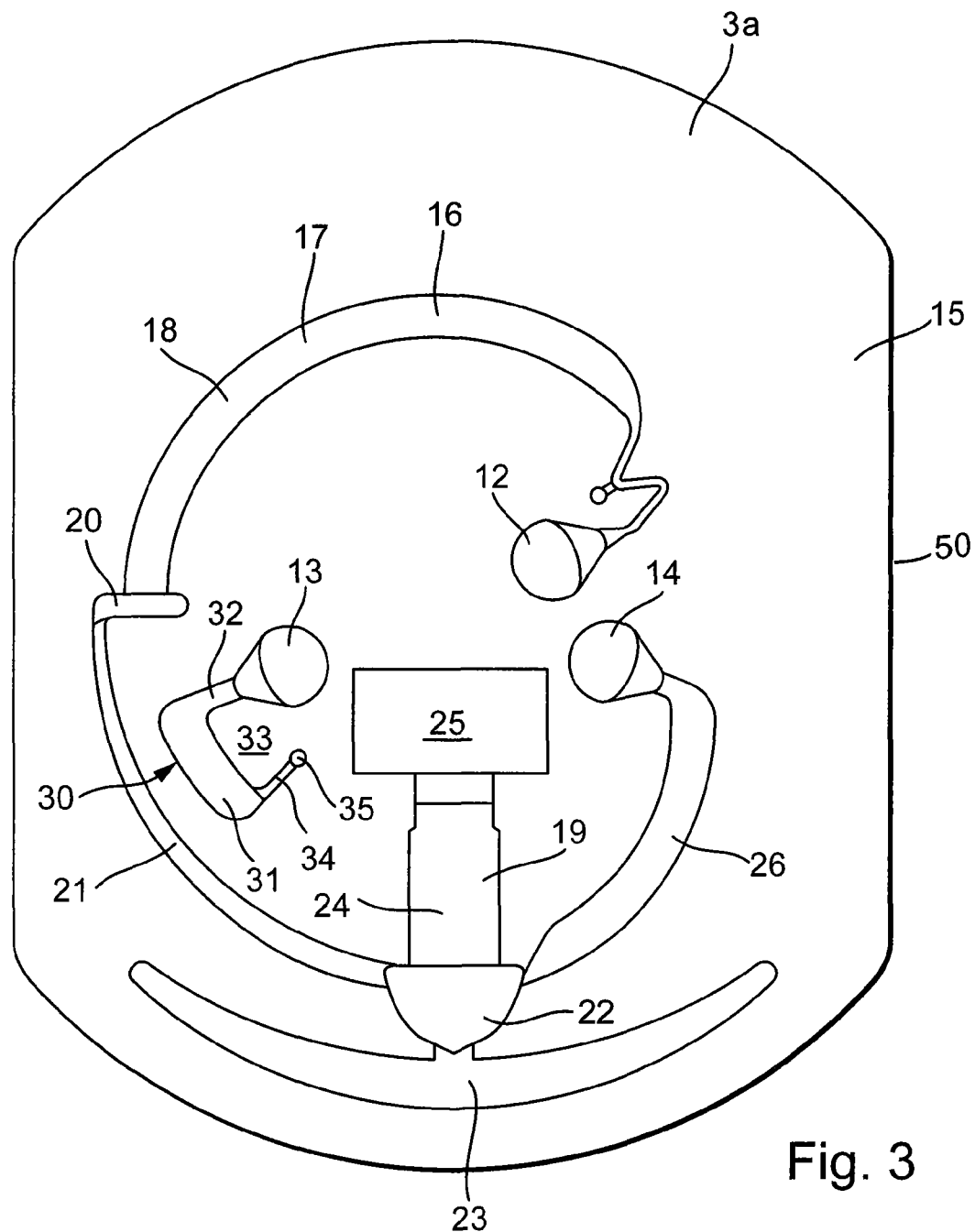
FIG. 3 shows a schematic illustration of a view of an embodiment of the test element from FIG. 2.
Figure 4:
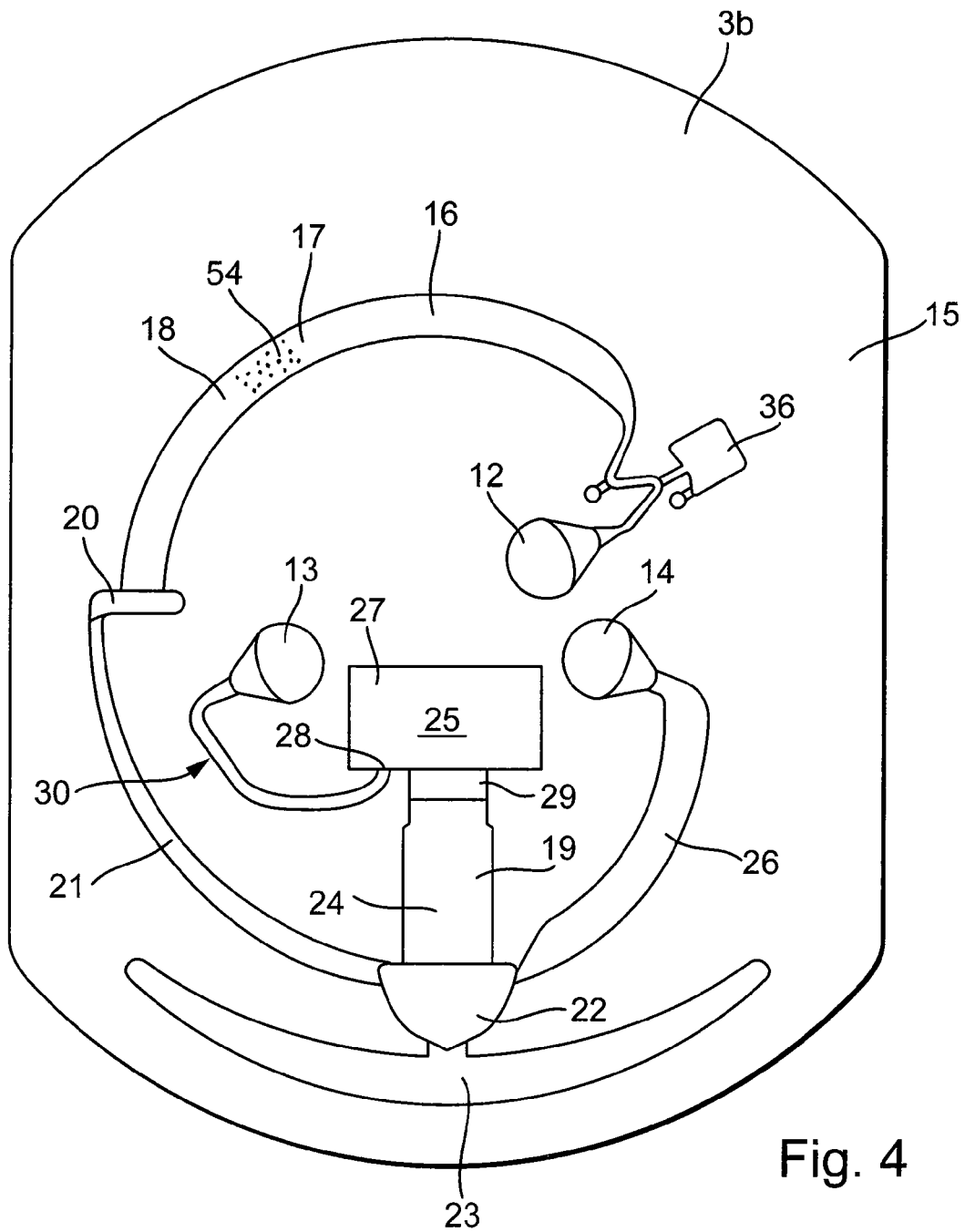
FIG. 4 shows a schematic illustration of a view of a further embodiment of the test element from FIG. 2.

The flushing or priming liquid flows through the flushing liquid supply opening 13 into an adjoining flushing liquid channel 32 and a flushing liquid collection chamber 31, in which the flushing liquid is disposed of, as shown in FIGS. 3 and 4.

After this preparatory flushing procedure, the test element 3 is rotated into its sample dispensing position, so that the sample liquid flowing through the dosing needle 10 dispenses into the sample supply opening 12. The sample liquid flows through the sample supply opening 12 in the sample analysis channel 16 to a measuring zone 19, in which the determination of the measurement variable characteristic for the analytical result is performed.

Figure 2:
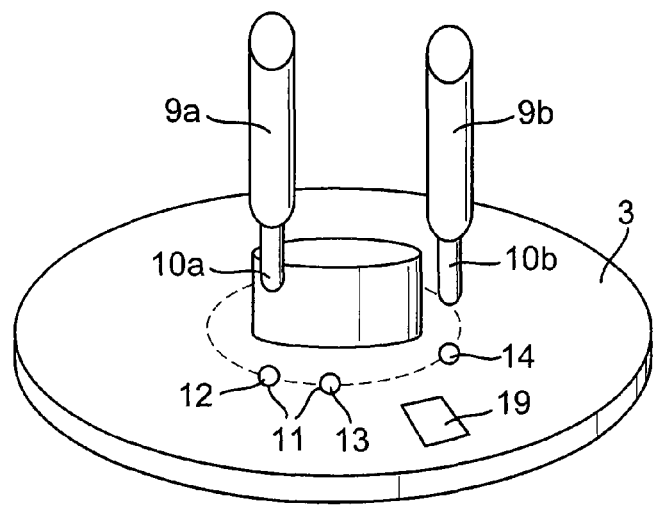
FIG. 2 shows a schematic illustration of the test element according to the invention.

FIG. 2 shows a detail of another embodiment of an analysis system 1 having a test element 3 and an analysis instrument 2 with two dosing stations 9a, 9b, each dosing station 9a, 9b having a dosing needle 10a, 10b.

The test element 3 has a sample supply opening 12, a flushing liquid supply opening 13 for receiving the flushing liquid, and a separate washing solution supply opening 14. In one embodiment, at least the distance of the flushing liquid opening 13 and the washing solution supply opening 14 from the rotation axis of the test element 3 is equal, so that all openings lie on an orbit of the test element 3 (proximal to the axis of rotation). In other embodiments, the distance of the three openings 12, 13, and 14 (as shown) are equal.

In one embodiment, the sample liquid is dispensed using the dosing needle 10a into the sample supply opening 12 and a washing solution is dispensed using the dosing needle 10b into the washing solution supply opening 14. Both dosing needles 10a, 10b are flushed using a flushing liquid before the first dosing, so that air bubbles escape from the dosing needles 10a, 10b and the needles are cleaned at the same time. The flushing liquid flows into the flushing liquid supply opening 13 after the flushing in each case. The dosing needles 10a, 10b advantageously do not have to be moved, because all supply openings lie on an orbit. A rotation of the test element 3 around the rotation axis, which in one embodiment extends through the center point or the center of the test element 3, positions the flushing liquid supply opening 13 below the dosing needle 10a, 10b to be flushed in each case. In another embodiment, it is possible to use the washing solution as a flushing liquid, wherein the quantity of the washing solution used for flushing is then disposed of in the priming structure (in the same manner as the flushing liquid is otherwise).

FIGS. 3 and 4 each show a schematic view of two embodiments of the test element, indicated by symbols 3a and 3b, respectively. The two test elements 3a, 3b each comprise a housing 15 having a substrate 50 (FIG. 3) and a central hole 52 (FIG. 1), which is used as a drive hole, for holding in the analysis instrument 2. In addition to the substrate 50, the disc-shaped test element 3a, 3b also typically contains a cover layer, which is not shown for the sake of clarity. The cover layer can fundamentally also carry fluidic structures, however, it will typically only have openings for delivering liquids or valve openings. Of course, instead of the central hole, a shaft can also be provided, around which the test element rotates. The rotation axis in one embodiment is positioned inside the test element, or in another embodiment outside the test element.

The housing 15 of the test elements 3a, 3b has fluidic or micro fluidic as well as chromatographic structures. The sample liquid, in particular whole blood, is delivered to the test element 3 via the sample supply opening 12. A sample analysis channel 16 comprises the sample supply opening 12 at its beginning and a measuring zone 19 at its end in the flow direction. A channel section 17, through which a liquid sample flows in the predefined flow direction to the measuring zone 19, extends between the sample supply opening 12 and the measuring zone 19. The liquid transport in the test element 3 occurs by capillary forces and/or centrifugal forces.

In the embodiment shown by FIG. 4, the sample supply opening 12 of the sample analysis channel 16 opens into a reservoir 36 which lies behind the opening 12 in the flow direction. A liquid sample flows into the reservoir 36 before it flows further in the channel section 17. The flowing and/or the flow velocity of the liquid sample can be influenced by suitable selection of the fluidic structures of the sample analysis channel 16. For example, in one embodiment the dimensions of the channel sections 17, 18, 21 is selected in such a manner that the occurrence of capillary forces is encouraged. In other embodiments, the surfaces of the channel sections is hydrophilized. The further flowing or filling of the individual channel sections of the sample analysis channel 16 can also only be made possible after the action of an external force, for example, in one embodiment a centrifugal force.

In still other embodiments, the different sections of the sample analysis channel 16 are dimensioned differently and/or provided for different functions. For example, in one embodiment a primary channel section 18 can contain a reagent system 54 (FIG. 4) reacting with the body fluid sample, of which at least one reagent in one embodiment is provided in dried or lyophilized form. It is also possible in another embodiment that at least one reagent is provided in liquid form, which is supplied to the test element 3a, 3b by dosing in one embodiment or pipetting in another embodiment. The test element 3a, 3b can have a reagent supply opening for this purpose. For example, in one embodiment the liquid reagent is applied using the same dosing system in which priming was (previously) performed.

The channel section 17 comprises a primary channel section 18, a capillary stop 20, and a secondary channel section 21. In one embodiment, the capillary stop 20 is implemented as a geometric valve or in another embodiment as a hydrophobic barrier. The secondary channel section 21 adjoining the capillary stop 20 guides a sample quantity measured off by the capillary stop 20. The quantity flowing through the capillary stop 20 is controlled by centrifugal forces using the rotational velocity of the test element 3.

At suitable rotational velocities, the separation of red blood cells or other cellular sample components is started in the secondary channel section 21. The reagents contained in the reagent system 54 of channel section 18, which are provided in dried form in one embodiment, are already dissolved upon entry of the sample liquid into the secondary channel section 21. Components of the sample-reagent mixture are captured in the collection zones 22 (plasma collection zone) and 23 (erythrocyte collection zone), which are implemented as chambers.

The measuring zone 19 adjoining the collection zone 22 in one embodiment includes a measuring chamber 24, which in one embodiment contains a porous, absorbent matrix. A waste chamber 25 is positioned after the measuring chamber 24 in the flow direction. In one embodiment, the reaction participants, sample components, and/or reagent components is disposed of in the waste chamber 25 after flowing through the measuring chamber 24.

The test element 3 has a priming structure 30, which comprises the flushing liquid supply opening 13, a flushing liquid collection chamber 31, and a flushing liquid channel 32 positioned between them. A valve 33 for ventilating the chamber, which comprises a ventilation channel 34 and a ventilation opening 35, is provided at the end of the flushing liquid collection chamber 31.

The exemplary embodiment of FIG. 3 clearly shows that the priming structure 30 is separated from all other channel structures of the test element 3a. It is also shown that the flushing liquid collection chamber 31 and the waste chamber 25 are separate and are not in fluid communication (do not have a fluid connection) to one another. The waste chamber 25 in one embodiment has a fluid connection to the measuring zone 19 in such a manner that it receives the liquid which has flowed through the measuring zone 19.

In addition, the washing solution supply opening 14, is shown in both embodiments of the test element 3a, 3b of FIGS. 3 and 4, respectively. A washing solution channel 26 adjoins to the washing solution supply opening 14. The washing solution channel 26, which in one embodiment includes the washing solution supply opening 14 at its beginning, and which in one embodiment is in fluid communication with the measuring zone 19 at its end such that a washing solution is suctioned through the washing solution channel 26 into the measuring chamber 24. The matrix of the measuring chamber 24 is washed and any excess, interfering reaction participants are removed. The washing solution subsequently also reaches the waste chamber 25.

In the embodiment according to FIG. 4, the test element 3b has a dual-function chamber 27, which in one embodiment is in fluid communication with the flushing liquid channel 32 and with the measuring zone 19 in such a manner that the dual-function chamber 27 is both flushing liquid collection chamber 31 and also waste chamber 25. A flushing liquid flowing into the flushing liquid supply opening 13 is conducted through the flushing liquid channel 32 into the dual-function chamber 27, which is then used as a flushing liquid collection chamber 31. A sample liquid and/or a sample liquid-reagent mixture or a washing liquid, each of which flows through the measuring zone 19, is also disposed of in the dual-function chamber 27, which then assumes the function of the waste chamber 25.

The dual-function chamber 27 has a first entry opening 28 and a second entry opening 29. Liquid flows out of the flushing liquid channel 32 into the dual-function chamber 27 through the first entry opening 28. The liquid, which comes out of the measuring zone 19 flows through the second entry opening 29 into the dual-function chamber 27.

Of course, the dual-function chamber 27 in one embodiment can also have only one entry opening, through which liquid enters. The liquid flows both from the flushing liquid channel 32 and also the measuring zone 19 through the entry opening. In this case, a waste channel adjoins the measuring zone 19, which has at least one section shared with the flushing liquid channel 32 and opens into the dual-function chamber 27.

By the above disclosure and figures various preferred exemplary embodiments of the present invention have been described. The technical features described above and shown by the figures can be used individually or in combination to provide other preferred designs of the invention. The exemplary embodiments shown in the drawings do not represent a restriction of the generality of the subject matter defined in the claims. As such, it will be apparent that modification and variations are possible without departing from the scope of the invention defined in the appended claims. For example, and not to be limited thereby, the invention can be applied to immunological sandwich assays and also to other analyses, in particular other types of immunoassays or other types of specific binding assays.

What is claimed is:

1. An analysis system for the analysis of a body fluid sample for an analyte contained therein, comprising:
    a test element having a housing and a sample analysis channel enclosed by the housing, the sample analysis channel including a sample supply opening and a measuring zone; and
    an analysis instrument having a dosing station for dosing a liquid into the test element, which is located on the analysis instrument, and having a measurement station for measuring a measurement variable, which is characteristic for an analytical result at the measuring zone of the test element, which is located in a measuring position,
    the test elements being adapted for reacting a body fluid sample supplied through the sample supply opening with a reagent system present in the sample analysis channel and whereby the reaction of the body fluid sample with the reagent system results in a change of the measurement variable characteristic for the analytical result in the measuring zone, and
    wherein the test element includes a flushing liquid supply opening, which is separate from the sample supply opening, and a flushing liquid collection chamber, and the flushing liquid supply opening and the flushing liquid collection chamber are in fluid communication to one another via a flushing liquid channel, the flushing liquid channel and the sample analysis channel being separate such that a liquid flowing through the flushing liquid channel does not reach the measuring zone.

2. The analysis system according to claim 1, wherein the test element is rotatable around an axis of rotation which extends through the test element.

3. The analysis system according to claim 2, wherein the sample supply opening and the flushing liquid supply opening are positioned at equal distance to the axis of rotation.

4. The analysis system according to claim 1, wherein the test element has a waste chamber, which is in fluid communication to the measuring zone in such a manner that it takes in liquid which has flowed through the measuring zone.

5. The analysis system according to claim 1, wherein the test element includes a dual-function chamber, which is in fluid communication to the flushing liquid channel and to the measuring zone in such a manner that it serves as both flushing liquid collection chamber and also a waste chamber of the test element.

6. The analysis system according to claim 5, wherein the dual-function chamber has a first entry opening, through which liquid flows from the flushing liquid channel into the dual-function chamber, and a second entry opening, through which liquid flows from the measuring zone into the dual-function chamber.

7. The analysis system according to claim 5, wherein the dual-function chamber has an entry opening, through which liquid enters both from the flushing liquid channel and also from the measuring zone.

8. The analysis system according to claim 1, wherein the measuring position of the test elements on the analysis instrument is identical to the sample dispensing position.

9. The analysis system according to claim 1, wherein the test element has a reagent supply opening, through which at least one reagent of the reagent system is supplied in liquid form to the sample analysis channel.

10. The analysis system according to claim 1, wherein at least one reagent of the reagent system is contained in solid form in the sample analysis channel.

11. The analysis system according to claim 1, wherein the flushing liquid collection chamber contains a porous, absorbent matrix.

12. The analysis system according to claim 1, wherein the test element additionally has a washing solution channel, which includes a washing solution supply opening and is in fluid communication with the measuring zone, the washing solution channel being separate from the flushing liquid channel and a washing solution flowing through the washing solution channel also flowing through the measuring zone.

13. The analysis system according to claim 1, wherein the measuring zone includes a measuring chamber, which contains a porous, absorbent matrix.

14. A test element for an analysis system providing an analysis of a body fluid sample for an analyte contained therein, comprising:
a housing;
a sample analysis channel enclosed by the housing, the sample analysis channel including a sample supply opening for receiving the body fluid sample, a reagent system for reacting with the received body fluid sample, and a measuring zone which provides a change of a measurement variable characteristic for an analytical result when the body fluid sample reacts with the reagent system;
a flushing liquid collection chamber positioned in the housing;
a flushing liquid supply opening separate from the sample supply opening; and
a flushing liquid channel providing fluid communication between the flushing liquid supply opening and the flushing liquid collection chamber,
wherein the flushing liquid channel and the sample analysis channel are separate such that a liquid flowing through the flushing liquid channel does not reach the measuring zone.

15. A test element for an analysis system providing an analysis of a body fluid sample for an analyte contained therein, comprising:
a housing;
a priming structure enclosed by the housing;
a sample analysis channel enclosed by the housing, the sample analysis channel including a sample supply opening and a measuring zone, the sample supply opening and the measuring zone being in fluid communication to one another via the sample analysis channel; and
a reagent system present in the sample analysis channel which reacts to the body fluid sample supplied through the sample supply opening and whereby the reaction of the body fluid sample with the reagent system results in a change of the measurement variable characteristic for the analytical result in the measuring zone, and
wherein the priming structure of the test element includes a flushing liquid supply opening and a flushing liquid collection chamber that are in fluid communication to one another via a flushing liquid channel, the flushing liquid channel and the sample analysis channel being separate such that a liquid flowing through the flushing liquid channel does not reach the measuring zone.

16. An analysis system for the analysis of a body fluid sample for an analyte contained therein, the analysis system comprising the test element according to claim 15 provided in an analysis instrument having a dosing station which doses the body fluid sample into the sample supply opening of the test element at a dosing position of the analysis instrument via a dosing needle, and a measurement station which measures the measurement variable characteristic for the analytical result at the measuring zone of the test element at a measuring position of the analysis instrument, wherein the dosing needle of the dosing station also delivers a washing solution to the test element via the flushing liquid supply opening which flows only through the flushing liquid channel to the flushing liquid collection chamber.

17. The analysis system according to claim 16, wherein the flushing liquid supply opening receives the washing solution from the dosing needle before the body fluid sample is dosed by the dosing needle into the sample supply opening.

* * * * *